(12) United States Patent
Bishop

(10) Patent No.: US 11,712,316 B2
(45) Date of Patent: Aug. 1, 2023

(54) STERILE SURGICAL AND RADIOLOGICAL DRAPE

(71) Applicant: Andrew Bishop, Cartersville, GA (US)

(72) Inventor: Andrew Bishop, Cartersville, GA (US)

( * ) Notice: Subject to any disclaimer, the term of this patent is extended or adjusted under 35 U.S.C. 154(b) by 516 days.

(21) Appl. No.: 16/994,819

(22) Filed: Aug. 17, 2020

(65) Prior Publication Data

US 2021/0045829 A1 Feb. 18, 2021

Related U.S. Application Data

(60) Provisional application No. 62/887,716, filed on Aug. 16, 2019.

(51) Int. Cl.
| | | |
|---|---|---|
| *A61B 6/00* | (2006.01) | |
| *A61B 46/10* | (2016.01) | |
| *A61B 46/20* | (2016.01) | |
| *A61B 6/04* | (2006.01) | |
| *A61B 50/30* | (2016.01) | |
| *A61B 50/00* | (2016.01) | |
| *A61B 6/10* | (2006.01) | |

(52) U.S. Cl.
CPC ............ *A61B 46/10* (2016.02); *A61B 6/0407* (2013.01); *A61B 6/4423* (2013.01); *A61B 6/4441* (2013.01); *A61B 46/20* (2016.02); *A61B 50/00* (2016.02); *A61B 50/30* (2016.02); *A61B 6/10* (2013.01); *A61B 2050/002* (2016.02)

(58) Field of Classification Search
CPC ..... A61B 46/00; A61B 6/4441; A61B 6/4423; A61B 6/10
See application file for complete search history.

(56) References Cited

U.S. PATENT DOCUMENTS

2013/0247921 A1* 9/2013 Dye ...................... A61B 46/00
128/853

* cited by examiner

*Primary Examiner* — Dani Fox
(74) *Attorney, Agent, or Firm* — Eversheds Sutherland (US) LLP

(57) ABSTRACT

Surgical and radiological drapes are provided herein. In some embodiments, a surgical drape is provided including a surgical table drape and a radiological drape including a first end portion attached to the surgical table drape, an enclosure portion configured to extend from the surgical table drape and enclose a radiological imaging unit and an adjustable closure mechanism configured to secure the upper portion about the radiological imaging unit, a side wall portion extending from the enclosure portion, and a second end portion comprising a weighted material.

16 Claims, 3 Drawing Sheets

STERILE SURGICAL AND RADIOLOGICAL DRAPE

CROSS-REFERENCE TO RELATED APPLICATIONS

This application claims the priority benefit of U.S. Provisional Application No. 62/887,716, filed Aug. 16, 2019, which is incorporated herein by reference.

FIELD OF THE DISCLOSURE

This disclosure relates to surgical drapes, specifically surgical radiological drapes.

BACKGROUND

During some types of surgeries, such as spinal and orthopedic surgeries, it is necessary to take radiological images of the patient's body while surgery is being performed. In order to take these radiological images, it is often necessary to introduce relatively large, unsterilized radiological equipment to the surgical theatre. For example, a C-arm fluoroscopy unit, which includes a large, generally C-shaped arm that allows the imaging portion of the unit to be adjusted into multiple positions during surgery by extending the arm beneath and through opposing sides of the operating table, is very commonly used. When using a C-arm fluoroscopy unit, however, the unit has an unsterilized portion of the C-arm on each side of the patient. Moreover, any distance below the knee or two feet from the ground is typically considered non-sterile. Therefore, items that go up and down, and in and out of the surgical field are of great concern.

Given the size and mobility of the C-arm unit, it is difficult to maintain sterility of the surgical field. Removable radiological drapes, such as C-ARMOR® radiological surgical drapes, available from TIDI Products, LLC, are designed to attach to a surgical table drape using removable attachment means like hook and loop, such as VELCRO® brand fasteners. These radiological drapes, however, often fail to adhere to the field, remain attached to a surgical table drape throughout a surgical procedure, and often fail to closely surround the C-arm unit, potentially compromising the sterility of the surgical field by failing to continuously cover the radiological imaging unit, or by overly extending into the non-sterile field. Prior art drapes may become unsterile and contaminate the sterile field such as when the C-arm is continuously raised and lowered, brushing the drape across the floor, after which the drape stays elevated or shifts upward on the machine instead of staying below the sterile field.

Accordingly, improved sterile surgical and radiological drapes are needed.

SUMMARY

This summary is provided to introduce various concepts in a simplified form that are further described below in the detailed description. This summary is not intended to identify required or essential features of the claimed subject matter nor is the summary intended to limit the scope of the claimed subject matter.

In one aspect, a surgical drape is provided including: a surgical table drape; and a radiological drape including a first end portion attached to the surgical table drape, an enclosure portion configured to extend from the surgical table drape and enclose a radiological imaging unit and an adjustable closure mechanism configured to secure the upper portion about the radiological imaging unit, a side wall portion extending from the enclosure portion, and a second end portion attached to the first end portion and comprising a weighted material.

In one aspect, a radiological drape is provided including a first end portion configured to be attached to a surgical table drape, an enclosure portion configured to extend from the surgical table drape and enclose a radiological imaging unit and an adjustable closure mechanism configured to secure the upper portion about the radiological imaging unit, a side wall portion extending from the enclosure portion, and a second end portion attached to the first end portion and comprising a weighted material.

DETAILED DESCRIPTION

Figure 1:
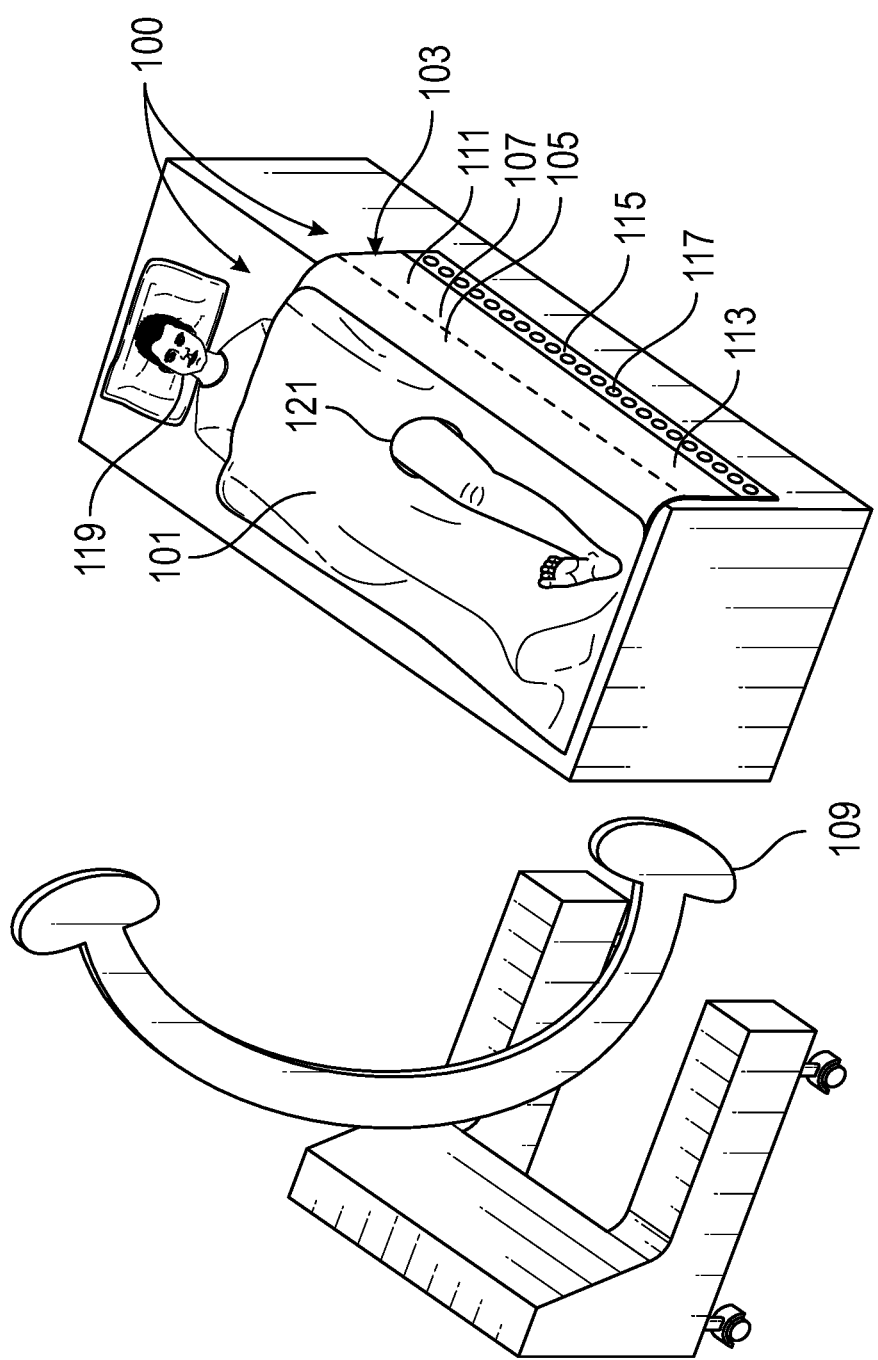
FIG. 1 illustrates a perspective view of a surgical drape and radiological imaging unit according to an embodiment of the present disclosure.

Surgical drapes and radiological drapes are disclosed herein. In some embodiments, a surgical drape is provided including a surgical table drape and a radiological drape. In some embodiments, the surgical table drape or radiological drape may be each made from a sterilized or sterilizable material. For example, in some embodiments, the surgical table drape and the radiological drape are made from the same material. In some embodiments, the surgical table drape and the radiological drape are mode from different materials. In some embodiments, the surgical table drape or the radiological drape are made from flexible materials. For example, in some embodiments, the surgical table drape and the radiological drape are made from nonwoven material or from a film. For example, the nonwoven material may be a spunlace, spunbond-meltblown-spunbond (SMS), or wet-laid material. In some embodiments, the nonwoven material may be made from a polyolefin, a polyamide, staple fibers such as wood pulp fibers, or any combinations thereof. For example, in some embodiments the polyolefin may include polyethylene, polypropylene, or combinations thereof. In some embodiments, the polyamide may include polyester, nylon, or any combinations thereof. In some embodiments, one or more of the surgical table drape and the radiological drape may be made from a polyolefin or polyamide film, such as a polyethylene film, polyester film, a multi-layered polyolefin film, and the like. In some embodiments, the radiological drape or a portion thereof is clear or substantially clear, so that, when in use with a radiological imaging unit, the radiological imaging unit can be easily seen and positioning easily adjusted.

In some embodiments, the radiological drape includes a first end portion attached to the surgical table drape. In some embodiments, the first end portion is permanently attached to the surgical table drape. As used herein, "permanently attached" is used broadly to refer to an attachment means which is not designed to be detached. For example, the first end portion of the radiological drape may be permanently attached to the surgical table drape by a permanent adhesive, heat bonding, or ultrasonic welding. In some embodiments, the first end portion is removably attached to the surgical table drape. As used herein, "removably attached" is used broadly to refer to an attachment means which can be removed without damaging the surgical table drape and/or the radiological drape. For example, in some embodiments the first end portion is removably attached to the surgical table drape using a zipper, or one or more clamps or clips.

In some embodiments, the radiological drape includes an enclosure portion configured to extend from the surgical table drape and enclose a radiological imaging unit. In some embodiments, the enclosure portion further includes an adjustable closure mechanism configured to secure the upper portion about the radiological imaging unit. For example, in some embodiments, the adjustable closure mechanism is an elastic or a drawstring. In some embodiments, the closure mechanism further comprises a toggle or other fastener. In some embodiments, the adjustable closure mechanism secures the enclosure portion using tension, such as by tension produced by an elastic band. In some embodiments, the enclosure portion may comprise two or more layers of material, joined together to form a passage for the adjustable closure mechanism. In some embodiments, the adjustable closure mechanism may be entirely enclosed within the enclosure portion, so that it cannot come into contact with the sterile field. For example, the adjustable closure mechanism may be an elastic which is completely enclosed by the enclosure portion. In some embodiments, the adjustable closure mechanism may be substantially enclosed within the enclosure portion, so that the majority of the adjustable closure mechanism cannot come into contact with the sterile field. For example, the adjustable closure mechanism may be a drawstring which is enclosed by the enclosure portion other than the draw portion or draw mechanism.

In some embodiments, the radiological drape includes a side wall portion extending from the enclosure portion. Without intending to be bound by any particular theory, it is believed that this side wall portion may further reduce the risk of the non-sterile radiological imaging unit would become separated from the radiological drape and potentially contaminate the sterile field.

In some embodiments, the radiological drape includes a second end portion including a weighted material. Specifically, the second end portion may be attached to an end of the side wall portion, may be attached to the enclosure portion, or may be attached to both the enclosure portion and the side wall portion. In some embodiments, the second end portion is made of at least two layers of material. For example, in some embodiments, the second end portion may completely enclose the weighted material, so that the weighted material cannot come into contact with the sterile field. The weighted material may include any material which, per square inch of the radiological drape, is heavier than the flexible material from which the radiological drape is made. For example, in some embodiments the weighted material may include one or more metal washers. In some embodiments, the radiological imaging unit is a radiological C-arm imaging unit.

Illustrated Embodiments

Figure 2:
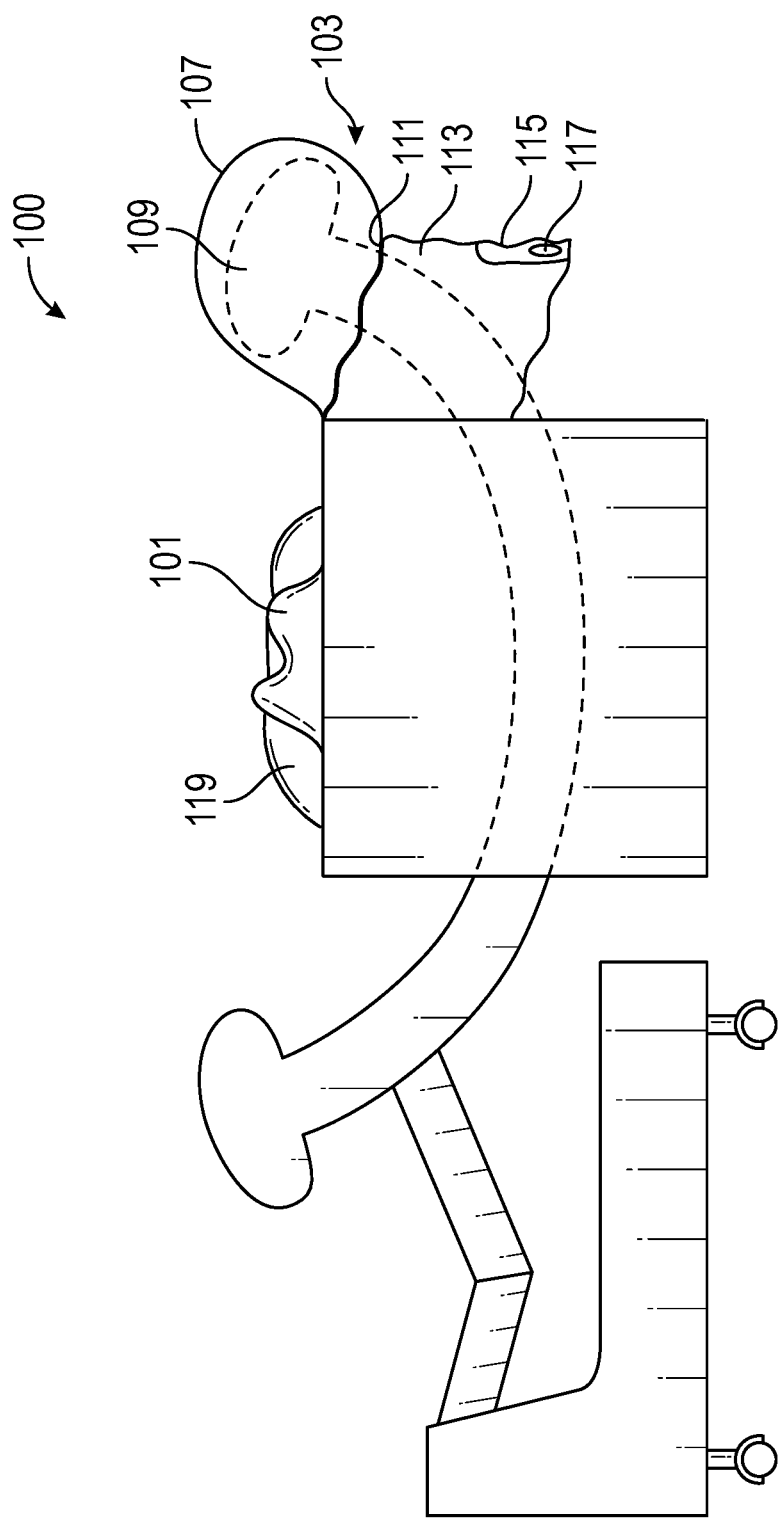
FIG. 2 illustrates a side view of the surgical drape and radiological imaging unit of FIG. 1 in a position to take an image of the body of a surgical patient.

FIG. 1 illustrates a surgical drape 100 according to an embodiment of the present disclosure. As illustrated in FIG. 1, the surgical drape 100 has been applied to a patient 119 being prepared for surgery. Specifically, a surgical table drape 101 has been applied over the patient, and a radiological drape 103 is in a closed or unextended position. The surgical table drape 101 may have an opening 121 for easier access to the surgical site on the patient. The surgical table drape 101 may cover the entire patient 119, except the surgical site on the patient; thus, the surgical table drape 101 may even cover the patient's head. Additionally, the surgical table drape 101 may hang off all four corners of the table. The surgical table drape 101 may be separate from the radiological drape 103, in which case the radiological drape 103 may be attached to the table. Alternatively, the radiological drape 103 may be removably or permanently attached to the surgical table drape 101. The radiological drape 103, may be the same length or a different length as the surgical table drape 101. During surgery, a radiological imaging unit 109, illustrated removed from the patient 119, may need to be used to properly visualize the surgical field, as illustrated in FIG. 2. The weighted material 117 in the second end portion 115 may be distributed across the entire length of the radiological drape 103, as shown in FIG. 1. Alternatively, the weighted material may be concentrated in one or more parts of the second end portion 115. The distribution of weighted material 117 may be even or uneven.

As illustrated in FIG. 2, the radiological imaging unit 109 may be passed underneath the surgical table drape 101 outside the sterile field. In order to maintain sterility of the surgical field, however, the portion of the radiological imaging unit 109 which may extend into the sterile field is covered by the radiological drape 103. Specifically, an enclosure portion 107 of the radiological drape 103 encloses the radiological imaging unit 109, with the aid of an adjustable closure mechanism 111, illustrated as a drawstring. A side wall portion 113 of the radiological drape 103 extends from the enclosure portion 107 and the adjustable closure mechanism 111, and is maintained in a substantially vertical orientation by a second end portion 115 which contains a weighted material 117. That is, the weighted material 117 in the second end portion 115 prevents the side wall portion 113 from inverting or "floating" up, which could compromise the sterile field by coming into contact with unsterile surfaces, or exposing the unsterile radiological imaging unit 109.

Figure 3:
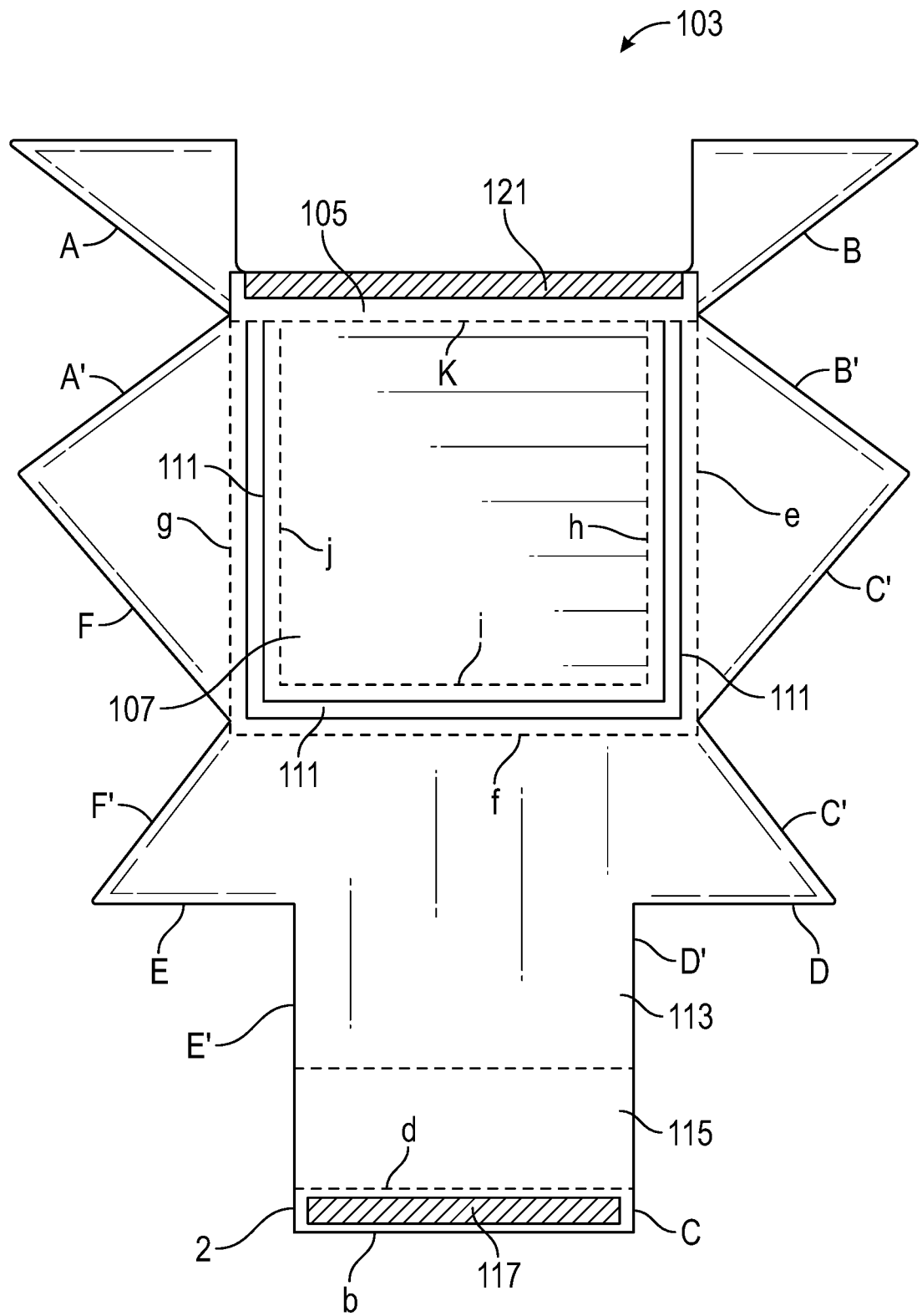
FIG. 3 illustrates the radiological drape of the surgical drape of FIGS. 1 and 2 in an unfolded or unassembled configuration.

FIG. 3 illustrates the radiological drape 103 of FIGS. 1 and 2 in an unfolded or unassembled configuration. In this illustrated embodiment, a single piece of flexible material is formed, wherein the respective edges A, A', B, B', C, C', D, D', E, E', F, and F' are joined, such as by a weld seam, to form the side wall portion 113 of the radiological drape 103. As illustrated in this figure, a first end portion 105 includes an adhesive 121 which is configured to attach the radiological drape 103 to a surgical table drape, or to the table (not shown). Further, the second end portion 115 includes a weighted material 117. In some embodiments, the second end portion 115 may be made from two layers of material, joined at edges a, b, and c, and at a seam d, such that the weighted material 117 is completely enclosed within the radiological drape 103. Similarly, in some embodiments the enclosure portion 107 may be made of two layers of material, joined at seams e, f, g, h, i, j, and k. In this way, the two layers of material may form a passage for containing the adjustable closure mechanism 111. For example, in some embodiments the adjustable closure mechanism 111 may be an elastic which is completely contained within the radiological drape 103. In some embodiments, the adjustable closure mechanism 111 may be a drawstring which is substantially enclosed in the radiological drape 103.

It will be understood by those skilled in the art that the dimensions of the surgical and/or radiological drape(s) may be varied depending on the size of the patient and the location of the surgical site on the patient, i.e., the type of surgery being performed. For example, if the patient is a child, the dimensions of the surgical drape may be decreased. FIG. 1 depicts a surgical table drape 101 and radiological drape 103 configured for surgery of a patient's left knee. Therefore, the opening 121 is positioned over the patient's left knee, and the leg has been pulled through the opening 121. It is understood that the opening 121 can be any shape, including a polygon, circle, or oval. It is understood that the surgical drape can be manufactured such that the opening 121 is located proximate to any surgical site, and thus the surgical table drape and 101 radiological drape 103 may be configured accordingly. For example, a surgical table drape and/or radiological drape configured for a right knee surgery might be a mirror image of the drapes depicted in FIG. 1. Thus, for a right knee surgery, the opening 121 would be over the right knee and the radiological drape 103 would hang from the opposite side of the table as the radiological drape 103 depicted in FIG. 1.

Table 1 includes example surgical drape dimensions for four different surgeries: a left hip surgery, a right hip surgery, a left knee surgery, and a right knee surgery. It is understood that manufactured drapes may have dimensions within ±25%, such as within ±10%, within ±5%, or within ±1% of the example dimensions below. It is understood that the dimensions may be adjusted to accommodate the specific size of a patient or the specific location of the surgery.

TABLE 1

| Surgery | Example dimensions |
| --- | --- |
| Left knee | drape height: 83.75"; drape width: 47.5"; opening (circular): 12" diameter; opening (square) 15" sides; edge of opening: 36" from bottom; edge of opening: 9" from right. |
| Right knee | drape height: 83.75"; drape width: 47.5"; opening (circular): 12" diameter; opening (square) 15" sides; edge of opening: 36" from bottom; edge of opening: 9" from left. |
| Left hip | drape height: 84"; drape width: 43.5"; opening (circular): 16" diameter; opening (square): 20" sides; edge of opening: 20" from top; edge of opening: 9" from right. |
| Right hip | drape height: 84"; drape width: 43.5"; opening (circular): 16" diameter; opening (square): 20" sides; edge of opening: 20" from top; edge of opening: 9" from left. |

While the disclosure has been described with reference to a number of embodiments, it will be understood by those skilled in the art that the invention is not limited to such disclosed embodiments. Rather, the invention can be modified to incorporate any number of variations, alterations, substitutions, or equivalent arrangements not described herein, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A surgical drape comprising:
   a surgical table drape; and
   a radiological drape comprising:
   a first end portion attached to the surgical table drape,
   an enclosure portion configured to extend from the surgical table drape and enclose a radiological imaging unit and an adjustable closure mechanism configured to secure the upper portion about the radiological imaging unit,
   a side wall portion extending from the enclosure portion, and
   a second end portion attached to the first end portion and comprising a weighted material.

2. The surgical drape of claim 1, wherein the first end portion is permanently attached to the surgical table drape.

3. The surgical drape of claim 2, wherein the first end portion is attached to the surgical table drape using an adhesive, ultrasonic bonding, or heat bonding.

4. The surgical drape of claim 1, wherein the first end portion is removably attached to the surgical table drape.

5. The surgical drape of claim 4, wherein the first end portion is attached to the surgical table drape by a zipper.

6. The surgical drape of claim 1, wherein the radiological imaging unit is a radiological C-arm imaging unit.

7. The surgical drape of claim 1, wherein the adjustable closure mechanism comprises elastic.

8. The surgical drape of claim 1, wherein the adjustable closure mechanism comprises a drawstring.

9. The surgical drape of claim 1, wherein the second end portion comprises a sealed pouch containing the weighted material.

10. The surgical drape of claim 1, wherein the weighted material comprises one or more metal washers.

11. A radiological drape comprising:
    a first end portion configured to be attached to a surgical table drape,
    an enclosure portion configured to extend from the surgical table drape and enclose a radiological imaging unit and an adjustable closure mechanism configured to secure the upper portion about the radiological imaging unit,
    a side wall portion extending from the enclosure portion, and
    a second end portion attached to the first end portion and comprising a weighted material.

12. The radiological drape of claim 11, wherein the radiological imaging unit is a radiological C-arm imaging unit.

13. The radiological drape of claim 11, wherein the adjustable closure mechanism comprises elastic.

14. The radiological drape of claim 11, wherein the adjustable closure mechanism comprises a drawstring.

15. The radiological drape of claim 1, wherein the second end portion comprises a sealed pouch containing the weighted material.

16. The radiological drape of claim 1, wherein the weighted material comprises one or more metal washers.

* * * * *